US006761728B2

(12) United States Patent
Harguth et al.

(10) Patent No.: US 6,761,728 B2
(45) Date of Patent: *Jul. 13, 2004

(54) REFORMING WET-TANTALUM CAPACITORS IN IMPLANTABLE DEFIBRILLATORS AND OTHER MEDICAL DEVICES

(75) Inventors: Robert S. Harguth, Ham Lake, MN (US); Ron Balczewski, Roseville, MN (US); William J. Linder, Golden Valley, MN (US); Gregory Scott Munson, Golden Valley, MN (US); Michael Wesley Paris, Maple Grove, MN (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/900,595

(22) Filed: Jul. 6, 2001

(65) Prior Publication Data

US 2001/0047190 A1 Nov. 29, 2001

Related U.S. Application Data

(63) Continuation of application No. 09/453,358, filed on Dec. 1, 1999, now Pat. No. 6,283,985.

(51) Int. Cl.[7] .............................................. A61N 1/00
(52) U.S. Cl. ....................................................... 607/1
(58) Field of Search .............................. 607/1, 2, 3, 4, 607/5, 6, 7, 8, 9

(56) References Cited

U.S. PATENT DOCUMENTS

| 3,828,227 | A | 8/1974 | Millard et al. ............. 317/230 |
| 4,067,786 | A | 1/1978 | Hilbert et al. ............ 204/56 R |
| 4,179,725 | A | 12/1979 | Maguire ...................... 361/433 |
| 4,571,662 | A | 2/1986 | Conquest et al. ........... 361/306 |
| 5,369,547 | A | 11/1994 | Evans ......................... 361/516 |
| 5,469,325 | A | 11/1995 | Evans ......................... 361/526 |
| 5,559,667 | A | 9/1996 | Evans ......................... 361/526 |
| 5,682,525 | A | 10/1997 | Bouve et al. ............... 395/615 |
| 5,737,181 | A | 4/1998 | Evans ......................... 361/504 |
| 5,754,394 | A | 5/1998 | Evans et al. ................ 361/516 |

(List continued on next page.)

FOREIGN PATENT DOCUMENTS

| WO | 90/14676 | 11/1990 | ............ H01G/9/02 |

OTHER PUBLICATIONS

Evans, D.A., "A 170 Volt Tantalum Hybrid Capacitor—Engineering Considerations", *Proceedings of the Seventh International Seminar on Double Layer Capacitors and Similar Energy Storage Devices*, Deerfield Beach, FL, 5 p., 1997).

(List continued on next page.)

*Primary Examiner*—Scott M. Getzow
(74) *Attorney, Agent, or Firm*—Michael F. Scalise (57) ABSTRACT

Miniature defibrillators and cardioverters detect abnormal heart rhythms and automatically apply electrical therapy to restore normal heart function. Critical components in these devices are aluminum electrolytic capacitors, which store and deliver one or more life-saving bursts of electric charge to a heart of a patient. This type of capacitor requires regular "reform" to preserve its charging efficiency over time. Because reform expends valuable battery life, manufacturers developed wet-tantalum capacitors, which are generally understood not to require reform. Yet, the present inventors discovered through extensive study that wet-tantalum capacitors exhibit progressively worse charging efficiency over time. Accordingly, to address this problem, the inventors devised unique reform techniques for wet-tantalum capacitors. One exemplary technique entails charging wet-tantalum capacitors to a voltage equal to about 90% of their rated voltage and maintaining this voltage for about five minutes before discharging them.

38 Claims, 3 Drawing Sheets

U.S. PATENT DOCUMENTS

| | | |
|---|---|---|
| 5,792,188 A | 8/1998 | Starkweather et al. ......... 607/5 |
| 5,861,006 A | 1/1999 | Kroll .............................. 607/5 |
| 5,899,923 A | 5/1999 | Kroll et al. ..................... 607/5 |
| 5,922,215 A | 7/1999 | Pless et al. ..................... 216/6 |
| 5,925,068 A | 7/1999 | Kroll ............................ 607/29 |
| 5,982,609 A | 11/1999 | Evans ........................ 361/516 |

OTHER PUBLICATIONS

Evans, D.A., "Hermetic Hybrid Capacitors (and Other Goodies)", *Proceedings of the Sixth International Seminar on Double Layer Capacitors and Similar Energy Storage Devices*, Deerfield Beach, FL, 6 p., (1996).

Evans, D.A., et al., "Hybrid Capacitor Applications", *Proceedings of the Eighth International Seminar on Double Layer Capacitors and Similar Energy Storage Devices*, Deerfield Beach, FL, 11 p., (1998).

FaradNet, "Electrolytic Capacitors Part 1: Chapter 2—Basic Theory of Operation of Electrolytic Capacitors", http://www.faradnet.com/deeley/chapt 02.htm, Current edition copyright by Tyra T. Buczkowski, 7 p., (1996).

Kaiser, Cletus J., "Tantalum Capacitors", *The Capacitor Handbook, 1st ed. Olathe, KS: CJ Pub.*, (1990), 79–87.

REFORMING WET-TANTALUM CAPACITORS IN IMPLANTABLE DEFIBRILLATORS AND OTHER MEDICAL DEVICES

CROSS REFERENCE TO RELATED APPLICATIONS

This application is a continuation of U.S. patent application Ser. No. 09/453,358, filed on Dec. 1, 1999 now U.S. Pat. No. 6,283,985, the specification of which is incorporated herein by reference.

BACKGROUND OF THE INVENTION

The present invention concerns capacitors, particularly wet-tantalum capacitors used in medical devices, such as implantable defibrillators, cardioverters, pacemakers, and more particularly methods of maintaining wet-tantalum capacitors in these devices.

Since the early 1980s, thousands of patients prone to irregular and sometimes life threatening heart rhythms have had miniature defibrillators and cardioverters implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The typical defibrillator or cardioverter includes a set of electrical leads, which extend from a sealed housing into the walls of a heart after implantation. Within the housing are a battery for supplying power, a capacitor for delivering bursts of electric current through the leads to the heart, and monitoring circuitry for monitoring the heart and determining when, where, and what electrical therapy to apply. The monitoring circuitry generally includes a microprocessor and a memory that stores instructions not only dictating how the microprocessor answers therapy questions, but also controlling certain device maintenance functions, such as maintenance of the capacitors in the device.

The capacitors are typically aluminum electrolytic capacitors. This type of capacitor usually includes strips of aluminum foil and electrolyte-impregnated paper. Each strip of aluminum foil is covered with an aluminum oxide which insulates the foils from the electrolyte in the paper. One maintenance issue with aluminum electrolytic capacitors concerns the degradation of their charging efficiency after long periods of inactivity. The degraded charging efficiency, which stems from instability of the aluminum oxide in the liquid electrolyte, ultimately requires the battery to progressively expend more and more energy to charge the capacitors for providing therapy.

Thus, to repair this degradation, microprocessors are typically programmed to regularly charge and hold aluminum electrolytic capacitors at or near a maximum-energy voltage (the voltage corresponding to maximum energy) for a time period less than one minute, before discharging them internally through a non-therapeutic load. (In some cases, the maximum-energy voltage is allowed to leak off slowly rather being maintained.) These periodic charge-hold-discharge cycles for maintenance are called "reforms." Unfortunately, the necessity of reforming aluminum electrolytic capacitors reduces battery life.

To eliminate the need to reform, manufacturers developed wet-tantalum capacitors. Wet-tantalum capacitors use tantalum and tantalum oxide instead of the aluminum and aluminum oxide of aluminum electrolytic capacitors. Unlike aluminum oxide, tantalum oxide is reported to be stable in liquid electrolytes, and thus to require no energy-consuming reforms. Moreover, conventional wisdom teaches that holding wet-tantalum capacitors at high voltages, like those used in conventional reform procedures, decreases capacitor life. So, not only is reform thought unnecessary, it is also thought to be harmful to wet-tantalum capacitors.

However, the present inventors discovered through extensive study that wet-tantalum capacitors exhibit progressively worse charging efficiency over time. Accordingly, there is a previously unidentified need to preserve the charging efficiency of wet-tantalum capacitors.

SUMMARY OF THE INVENTION

To address this and other needs, the inventors devised methods of maintaining wet-tantalum capacitors in implantable medical devices. One exemplary method entails reforming this type of capacitor. More particularly, the exemplary method entails charging wet-tantalum capacitors to a high voltage and keeping the capacitors at a high voltage for about five minutes, before discharging them through a non-therapeutic load. In contrast to conventional thinking, reforming wet-tantalum capacitors at least partially restores and preserves their charging efficiency.

Another facet of the invention includes an implantable medical device, such as defibrillator, cardioverter, cardioverter-defibrillator, or pacemaker, having one or more wet-tantalum capacitors and means for reforming the capacitors. Yet another facet includes a computer-readable medium bearing instructions for reforming wet-tantalum capacitors.

DESCRIPTION OF THE PREFERRED EMBODIMENTS

Figure 1:
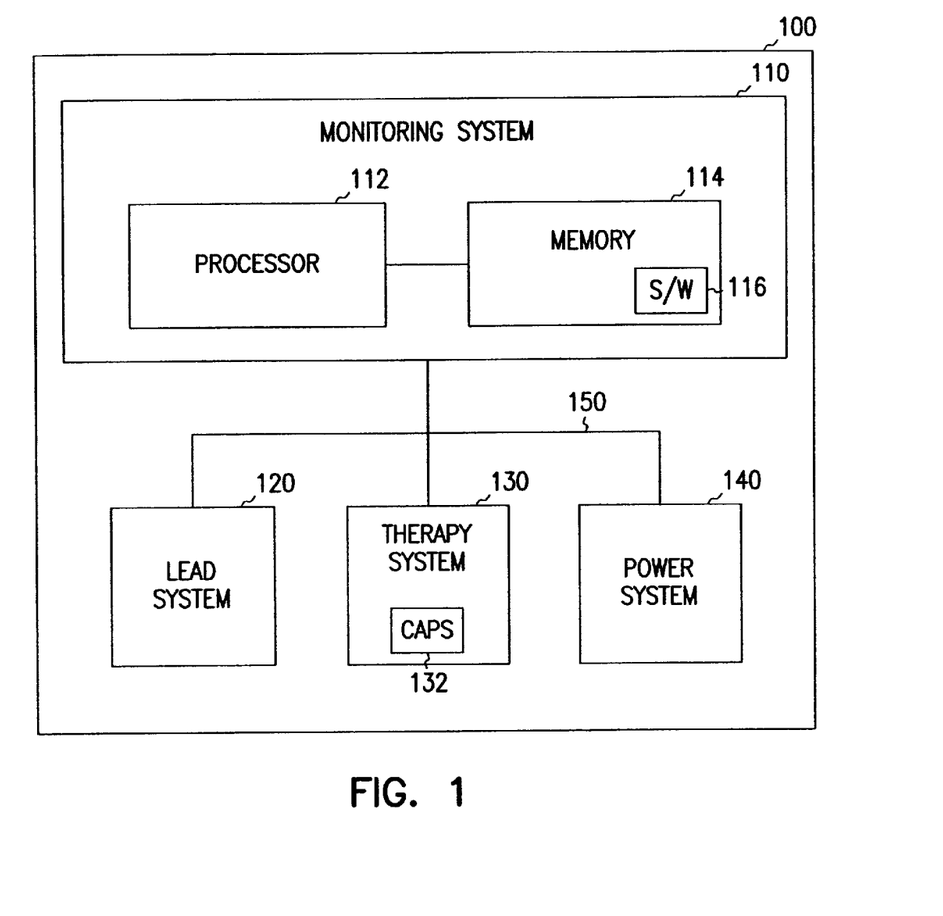
FIG. 1 is a block diagram of an exemplary implantable heart monitor incorporating teachings of the present invention.
Figure 2:
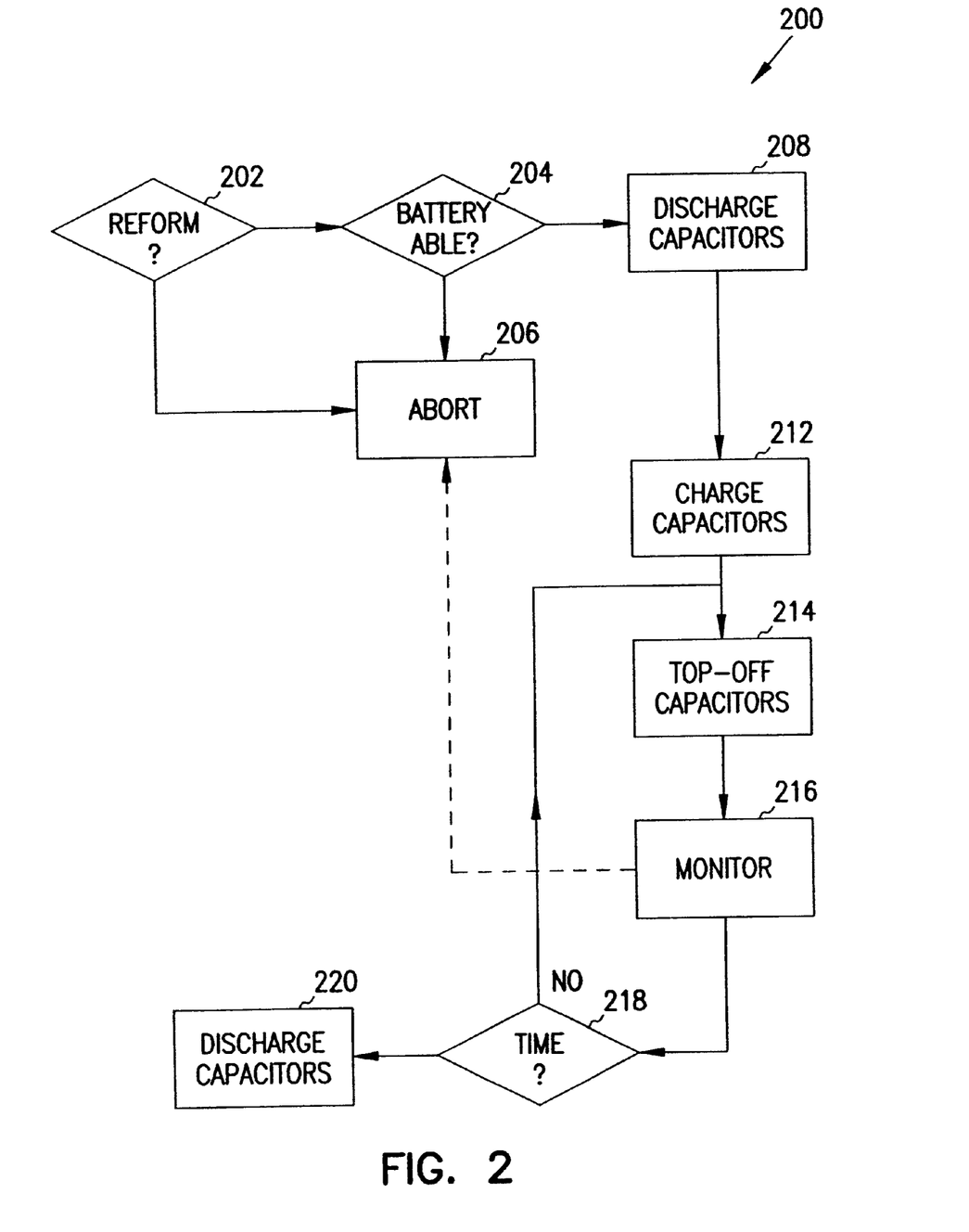
FIG. 2 is a flow chart illustrating exemplary operation of the heart monitor of FIG. 1.
Figure 3:
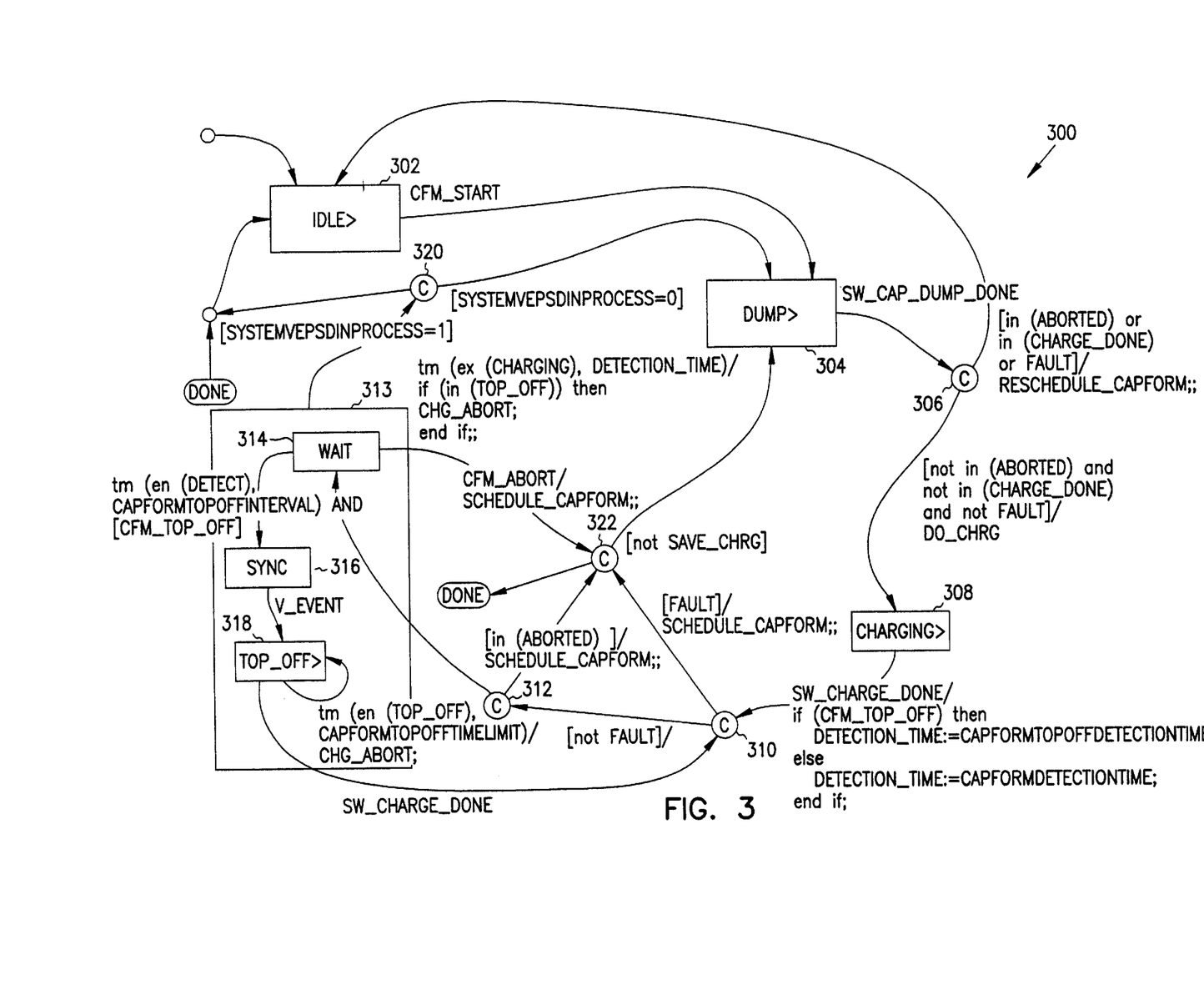
FIG. 3 is a state flow diagram illustrating an alternative operation of the heart monitor of FIG. 1.

The following detailed description, which references and incorporates FIGS. 1–3, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

FIG. 1 shows an exemplary implantable heart-monitoring device (or pulse generator) 100 incorporating teachings of the present invention. Device 100 includes a monitoring system 110, a lead system 120, a therapy system 130, a power system 140, and an interconnective bus 150. Monitoring system 110 includes a processor or microcontroller 112 and a memory 114. Memory 114 includes one or more software modules 116 which store one or more computer instructions in accord with the present invention. Some embodiments of the invention replace software modules 116 with one or more hardware or firmware modules. In the exemplary embodiment, processor 112 is similar to a ZiLOG™ Z80 microprocessor (with a math coprocessor), and memory 114 is a random-access memory. However, the invention is not limited to any particular microprocessor, microcontroller, or memory.

Lead system 120, in the exemplary embodiment, includes one or more electrically conductive leads—for example, atrial, ventricular, or defibrillation leads—suitable for insertion into a heart. One or more of these are suitable for sensing electrical signals from a portion of the heart and one or more are suitable for transmitting therapeutic doses of electrical energy. Lead system 120 also includes associated sensing and signal-conditioning electronics, such as atrial or ventricular sense amplifiers and/or analog-to-digital converters, as known or will be known in the art.

In some embodiments, lead system 120 supports ventricular epicardial rate sensing, atrial endocardial bipolar pacing and sensing, ventricular endocardial bipolar pacing and sensing, epicardial patches, and Endotak® Series and ancillary leads. In some embodiments, lead system 120 also supports two or more pacing regimens, including DDD pacing. Also, some embodiments use at least a portion of a housing of device 100 as an optional defibrillation electrode. The invention, however, is not limited in terms of lead or electrode types, lead or electrode configurations, pacing modes, sensing electronics, or signal-conditioning electronics.

Therapy system 130 includes a capacitor system 132 and other circuitry (not shown) for delivering or transmitting electrical energy in measured doses through lead system 120 to a heart or other living tissue. Additionally, therapy system 130 includes one or more timers, analog-to-digital converters, and other conventional circuitry (not shown) for measuring various electrical properties related to performance, use, and maintenance of the therapy system.

In the exemplary embodiment, capacitor system 132 include three or four, flat or cylindrical, wet-tantalum capacitors. The exemplary wet-tantalum capacitors comprise a tantalum metal anode, $Ta_2O_5$ dielectric, a liquid electrolyte, and a cathode of material other than tantalum, for example, $RuO_2$. Capacitors of this description are known in the trade as hybrid capacitors, with some versions having tantalum cases and others having polypropylene cases. See also U.S. Pat. Nos. 5,982,609; 5,469,325; 5,737,181; and 5,754,394, which are incorporated herein by reference.

Exemplary capacitor specifications are 185 volts surge, 60 microamp leakage current at 175 volts, 90 microamp leakage current at 185 volts, an AC capacitance of 490 microfarads, and equivalent series resistance (ESR) of 1.2 ohms. Capacitors meeting these or specifications or having similar construction are manufactured by Wilson Greatbatch Ltd. of Clarence, N.Y. or Evans Capacitor Company of East Providence, R.I.

In general operation, lead system 120 senses atrial or ventricular electrical activity and provides data representative of this activity to monitoring system 110. Monitoring system 110, specifically processor 112, processes this data according to instructions of software module 116 of memory 114. If appropriate, processor 112 then directs or causes therapy system 130 to deliver one or more measured doses of electrical energy or other therapeutic agents through lead system 120 to a heart. Additionally, software module 116 includes one or more instructions or code segments which manage and maintain capacitors 132 in accord with teachings of the inventions.

FIG. 2, which shows an exemplary flow chart 200, illustrates an exemplary capacitor-management method embodied within software module 116 and executed by processor 112 and other relevant portions of device 100. Flow chart 200 includes blocks 202–220, which are arranged serially in the exemplary embodiment. However, other embodiments of the invention may execute two or more blocks in parallel using multiple processors or a single processor organized as two or more virtual machines or subprocessors. Moreover, still other embodiments implement the blocks as two or more specific interconnected hardware modules with related control and data signals communicated between and through the modules. Thus, the exemplary process flow applies to software, firmware, and hardware implementations.

In process block 202, processor 112 of device 100, determines whether to initiate reform of the wet-tantalum capacitors. The exemplary embodiment makes this determination based on whether a predetermined amount of time, for example 30, 60, 90, or 120 days, has elapsed since the last reform or the last therapeutic use, that is, charge and discharge, of the capacitor. Some embodiments use a timer to support this determination, with the timer in some embodiments being reset with every therapeutic use or certain therapeutic uses of the capacitors and other embodiments ignoring therapeutic use of the capacitor as a factor influencing reform timing. Other embodiments trigger or schedule reform based on thresholding of certain average or instantaneous performance aspects of the capacitors, such as actual or estimated full-energy charge time. And still other embodiments initiate reform as part of an overall storage mode. See also U.S. Pat. No. 5,899,923 which is entitled Automatic Capacitor Maintenance System for an Implantable Cardioverter Defibrillator and which is incorporated herein by reference.

If the processor determines that reform is presently undesirable, execution proceeds to block 206, where the reform procedure is aborted. In the exemplary embodiment, aborting the reform procedure entails rescheduling it for some programmable amount of time in the future, for example 23–25 hours later. However, if the processor determines that reform is presently desirable, execution proceeds to block 204.

In block 204, the processor assesses whether the battery is in condition to execute the exemplary capacitor reform procedure. In the exemplary embodiment, this entails measuring the open-circuit battery voltage and determining whether the battery has reached the end of its life or whether the battery has reached an elective-replacement state. The system deems the battery to have an end-of-life status when the last recorded capacitor charge time exceeds a predetermined charge time, such as 30 seconds, or it has an open-circuit voltage less than 2.1 volts. The system deems the battery to be in an elective-replacement state when its last recorded charge time exceeds 20 seconds or its open-circuit voltage is less than or equal to a specific voltage, such as 2.45 volts. If the battery cannot execute the reform procedure, execution of the capacitor reform procedure is aborted at block 206 to conserve energy. On the other hand, if it can execute reform, execution continues at block 208.

In block 208, the processor discharges the capacitors to allow an accurate measurement of charge time during subsequent procedures. In the exemplary embodiment, the discharge begins on the first cardiac cycle after initiation of the reform procedure and may require as much as two seconds to complete. The exemplary embodiment discharges the capacitors through a 1000-ohm load resistor. However, the invention is not limited to any particular discharge load or rate.

Block 212 entails charging the capacitors to a high voltage. (Some embodiments include enter a tachy-off mode prior to charging the capacitors.) The exemplary embodiment charges the capacitors to a high voltage about 5–15% less than their maximum-energy voltage to avoid or reduce the risk of accelerating aging of the capacitors; however, other embodiments charge the capacitors to their fill rated voltage. In addition, charging begins 90–110 milliseconds after the next cardiac cycle and ends when the capacitor voltage reaches the maximum-energy voltage. (In devices that use blanking intervals, the initiation of charging should fall within a blanking interval to reduce the risk of false arrhythmia detections.) When charging is completed, the exemplary embodiment records the elapsed charge time in memory.

In block 214, the processor further charges, or tops off, the capacitors to maintain the capacitors at a sufficiently high voltage for reform. In the exemplary embodiment implements an N-second top-off procedure which entails changing the sensed refractory period to 250 milliseconds and charging for an M-millisecond period on each cardiac cycle that occurs during the N-second period. N and M are programmable to any desired value; exemplary values for N and M are 5 and 200, respectively.

In some other embodiments, execution of the top-off procedure is contingent on whether the measured capacitor voltage is within a specific voltage range. In one embodiment, this entails determining whether the capacitor voltage is greater than the maximum-energy voltage less 10 volts per capacitor in the capacitor system. For example, in a one-capacitor system having a maximum-energy voltage of 185 volts, this embodiment tops off the capacitor when its voltage falls below 175 volts.

After topping off the capacitors, execution proceeds to block 216, to begin an L-second monitoring period. On the first cardiac cycle of this period, the system changes the sensed refractory back to its normal (pre-reform) setting, enabling detection of abnormal rhythms. If an abnormal rhythm is detected, the system aborts the reform procedure and addresses the abnormal rhythm. The exemplary embodiment sets L to 10; however, in general, this value is programmable. If an abnormal heart rhythm or heart condition requiring device therapy is detected, execution branches to block 206 to abort the reform procedure. However, if no condition requiring therapy is detected during the L-second period, execution proceeds to block 218.

In block 218, the processor determines whether the capacitors have been at the high voltage for a sufficiently long time period to effect reform of their tantalum oxide. The exemplary embodiment uses a default period in the range of about five minutes as a sufficiently long time period. If sufficient time has not elapsed, execution branches back to block 214. Other embodiments use periods in the range of 15 seconds to 10 minutes. (In conventional therapeutic use, capacitors typically hold their charge for a period in the range of 20 milliseconds to 10 seconds, before initiating a therapeutic discharge.)

In other embodiments, the sufficient amount of time is based on measured electrical properties of the capacitor system. For example, one embodiment bases the determination on whether the capacitor leakage current has fallen below a certain threshold. To determine a value or proxy for the capacitor leakage current, this embodiment monitors an actual or average time between successive top-offs, with each top-off initiated when the capacitor voltage falls below a certain voltage level. In any event, if the processors determines that a sufficient amount of time has elapsed, the processor executes block 220.

Block 220 entails initiating or allowing discharge of the one or more capacitors through a non-therapeutic load. (As used herein, discharge through a non-therapeutic load includes any discharge internal to the device as well as potential discharges at non-therapeutic levels or rates through the lead system.) The exemplary embodiment discharges the one or more capacitors through a 1000-ohm resistor; however, other embodiments allow the charge to dissipate through system leakage. Still other embodiments allow the one or more capacitors to float for some time, for example, 60 seconds, before initiating discharge through a load resistor. Thus, the invention is not limited to any particular mode, method, or technique of non-therapeutic discharge.

FIG. 3, which shows an exemplary state flow diagram 300, illustrates an alternate exemplary capacitor-management method embodied within software module 116 and executed by processor 112 and other relevant portions of device 100. Diagram 300 includes states or blocks 302–322. The exemplary diagram, drawn using commercially available simulation software with a state-diagram capability, uses the following definitions:

CFM_START denotes a request to start the capacitor reformation. The request is made with CFM_TOP_OFF set either true or false, depending on the number of elapsed days since the last successful capacitor reformation conducted with the top-off of the capacitors to ensure effective reform.

CFM_TOP_OFF denotes a parameter set the requester of the reform and determines if the reform will involve use of top off cycles or not.

SAVE_CHRG, which is normally set to false, controls whether any charge in the capacitor system is retained to treat a detected arrythmia. If an episode results in an abort of the capacitor reform, an abort function sets it true.

SCHEDULE_CAPFORM, which effects the abort functions, requests that a capacitor reform be run again within 24 hours or other specified time. The rescheduled reform will be same type as the aborted reform. For example, if the aborted reform used or was intended to use top off, the rescheduled reform will also use top off.

CAPFORMTOPOFFDETECTIONTIME denotes the desired value of the DETECTIONTIME when the reform uses top-off. In the exemplary embodiment, this value defaults to five minutes; however, in general, it lies in the range of 15 seconds to 10 minutes or 61 seconds to 10 minutes.

CAPFORMDETECTIONTIME denotes the desired value of reform conducted without use of top-off. The default value in the exemplary embodiment is zero.

CAPFORMTOPOFFINTERVAL denotes the top-off cycle time.

CHG_ABORT denotes the function of stopping the charging process.

CHG_DONE is a hardware signal indicating completion of a charging operation.

DETECTION_TIME equals CAPFORMTOPOFFDETECTIONTIME or CAPFORMDETECTIONTIME depending on the value of CFM_TOP_OFF.

V_EVENT denotes a detection of a ventricular sense, pace or no-sense timeout. However, more generally it denotes a detection of a cardiac event.

SW_CP_DUMP_DONE is a hardware signal denoting completion of a charge dump.

The exemplary state diagram also makes use of the following nomenclature: tm=timeout; en=enter; ex=exit. Thus, for example, tm(ex(CHARGING), DETECTION_TIME)

means that when the DETECTION_TIME elapses after exiting the CHARGING state a timeout will occur, triggering the associated path to be traversed and the state to change.

The alternate exemplary method begins at idle state block 302. During this state, the processor checks every 24 hours to see if it is time to reform. This entails determining whether it is time to perform a scheduled reform. For example, one can schedule a reform every 90 days. Depending on the value of CFM_TOP_OFF, the reform may or may not involve use of top offs of the capacitor to maintain capacitor voltage at a high voltage. Reforms with top off are done every 90 days in some embodiments.

At state 304, charge in the capacitor system is dumped. Dumping the charge facilitates accurate measurement of charging times. The hardware signal SW_CAP_DUMP_DONE signals completion of the dump and initiates transition to decision state (or block) 306.

At block 306, the processor determines if an abort signal or a fault, such as a failed dump, has occurred. If so, the RESCHEDULE_CAPFORM function is invoked. If not, a transition to charging state 308 occurs. In this state, the capacitors are initially charged to their maximum-energy voltage. The hardware signal SW_CHARGE_DONE indicates completion of the charging and initiates transition to decision block 310.

In decision block 310, the processor checks for a charge-time-fault or high-voltage on leads indicating leak. The charge-time fault indicates that too much time has elapsed without bringing the capacitors to full charge, suggesting a leak in the system. If there is not fault, a transition to decision block 312 occurs. In block 312, the processor checks for an external abort signal. One example of an activity that would result in the external abort signal is the use of telemetry to reprogram the device.

A fault at block 310 or an abort signal at block 312 forces a transition to decision block 322. At block 322, the processor decides whether to save the charge in the capacitors or to dump their charge, based on the value of SAVE_CHRG. With no fault at blocks 310 and 312, a transition to monitor state 313 occurs. Monitor state 313, which represents a parent state, includes three child states: wait state 314, sync state 316, and top-off state 318. The processor essentially stays at monitor state 313 until the reform is completed or aborted.

More specifically, the transition to monitor state 313 enters wait, or delay, state 314. Wait state 314 waits for a period of time, such as 10 seconds. This time is denoted CAPFORMTOPOFFINTERVAL. During this time, the device essentially looks for arrhythmia episodes. In an episode occurs, the reform is aborted and rescheduled and there is a transition to decision block 322. If no episode occurs, expiration of the time period (CAPFORMTOPOFFINTERVAL) results in a transition to sync state 316. Sync state 316 waits for the ventricular event, for example, a V-pace, V-sense, or no-sense timeout, before transitioning to top-off state 318, during which the capacitors are topped off.

In one version of this alternate implementation, the top off voltage level is 38 volts less than the voltage for maximum energy for a four-capacitor system. This is to ensure the capacitors are never over charged. Top off cycles are performed every CAPFORMTOPOFFINTERVAL seconds (2–65535 sec) for a duration determined by CAPFORMTOPOFFDETECTIONTIME (0–65535 sec). No top off cycle is allowed to charge for more than CAPFORMTOPOFFTIMELIMIT (2200–65535 ms). Each top off charge cycle is started synchronous to a ventricular event to ensure the charge circuit is activated during a refractory period.

After the preset DETECTION TIME has expired, there is a transition from monitor state 313 to decision block 320. Decision block 320 transitions to dump block 304 to dump the charge on the if no arrhythmia episode is in progress.

Conclusion

In furtherance of the art, the inventors have not only discovered the need to reform wet-tantalum capacitors in implantable medical devices, but also devised suitable reform methods and software. The exemplary method conducts reform every 90 days regardless of intervening therapeutic events, with reform entailing holding one or more wet-tantalum capacitors at a high voltage (within 10 percent of the rated capacitor voltage) for about five minutes. Other embodiments reform hybrid capacitors in medical devices generally and hold high-voltage charges on capacitors for times greater than one minute. Other applications for the invention include non-medical devices that require or would benefit from long-term stability of the charging efficiency of wet-tantalum capacitors.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A method of maintaining one or more wet-tantalum capacitors in an implantable medical device, with each capacitor having a rated voltage or a maximum-energy voltage, the method comprising:

maintaining at least one of the wet-tantalum capacitors at a high voltage relative its rated voltage or maximum-energy voltage for a time; and discharging, after the time, the one of the wet-tantalum capacitors through a non-therapeutic load, wherein discharging includes:

allowing the one of the wet-tantalum capacitors to float for a first time period; and discharging the one or more of the wet-tantalum capacitors through a non-therapeuitic load after expiration of the first time period.

2. The method of claim 1, wherein the high voltage is about 90 percent of the rated voltage or a maximum-energy voltage for the capacitors.

3. The method of claim 1, wherein the implantable medical device has a housing and the non-therapeutic load is a resistor within the housing.

4. The method of claim 1, wherein the one wet-tantalum capacitor comprises a tantalum anode and a non-tantalum cathode.

5. The method of claim 1 further including determining a value related to a capacitor leakage current, wherein the time is based on the value related to the capacitor leakage current.

6. The method of claim 1, wherein the time is greater than or equal to 15 seconds.

7. The method of claim 1, wherein the implantable device functions as a defibrillator, a cardioverter, or a pacemaker.

8. The method of claim 1, wherein each of the one or more capacitors has a 185-volts surge rating, a first nominal leakage-current rating of about 60 microamps at about 175 volts, a second nominal leakage-current rating of about 90 microamps at about 185 volts, an AC capacitance of about 490 microfarads, and an equivalent-series resistance of about 1.2 ohms.

9. The method of claim 1, wherein the first time period is about 60 seconds.

10. The method of claim 1:
wherein the implantable device includes a lead system for coupling to living tissue; and
wherein discharging the one wet-tantalum capacitor through the non-therapeutic load comprises discharging the one wet-tantalum capacitor through the lead system at a non-therapeutic level.

11. A method of maintaining one or more wet-tantalum capacitors in an implantable medical device, with each capacitor having a rated voltage, the method comprising:
maintaining at least one of the wet-tantalum capacitors at a high voltage relative its rated voltage for a time greater than or equal to 15 seconds;
discharging, after the time, the one or more of the wet-tantalum capacitors, wherein discharging includes:
allowing the one of the wet-tantalum capacitors to float for a first time period; and
discharging the one or more of the wet-tantalum capacitors through a non-therapeuitic load after expiration of the first time period.

12. The method of claim 11, wherein the high voltage is about 90 percent of the rated voltage.

13. The method of claim 11, wherein the one wet-tantalum capacitor comprises a tantalum anode and a non-tantalum cathode.

14. The method of claim 11, wherein the first time period is about 60 seconds.

15. The method of claim 11, wherein the implantable device includes a lead system for coupling to living tissue; and
wherein discharging the one wet-tantalum capacitor through the non-therapeutic load comprises discharging the one wet-tantalum capacitor through the lead system at a non-therapeutic level.

16. A method of maintaining one or more wet-tantalum capacitors in an implantable medical device, with each capacitor having a rated voltage, a tantalum anode, and a non-tantalum cathode, the method comprising:
maintaining at least one of the wet-tantalum capacitors at a voltage equal to about 90% of its rated voltage for a time of about five minutes;
discharging, after the time, the one or more of the wet-tantalum capacitors, wherein discharging includes:
allowing the one of the wet-tantalum capacitors to float for a first time period; and
discharging the one or more of the wet-tantalum capacitors through a non-therapeuitic load after expiration of the first time period.

17. The method of claim 16, wherein the implantable device includes a lead system for coupling to living tissue; and
wherein discharging the one wet-tantalum capacitor through the non-therapeutic load comprises discharging the one wet-tantalum capacitor through the lead system at a non-therapeutic level.

18. An implantable heart rhythm management device comprising:
one or more leads for sensing electrical signals of a patient or for applying electrical energy to the patient;
a monitoring circuit for monitoring heart activity of the patient through one or more of the leads; and
a therapy circuit for delivering electrical energy through one or more of the leads to a heart of the patient, wherein the therapy circuit includes a capacitor system having one or more wet-tantalum capacitors, each having a rated voltage;
means for maintaining at least one of the wet-tantalum capacitors at a high voltage relative its rated voltage for a time greater than or equal to about 5 minutes; and
means for discharging, after the time, the one or more of the wet-tantalum capacitors through a non-therapeutic load.

19. The implantable heart rhythm management device of claim 18 wherein the means for maintaining at least one of the wet-tantalum capacitors at a high voltage includes:
means for determining a charge time or leakage current of the one wet-tantalum capacitor;
means, responsive to the means for measuring, for charging the one capacitor to the high voltage when the determined charge time or leakage current exceeds a threshold; and
means for topping off the one capacitor.

20. The device of claim 19, wherein the charge time corresponds to a time for charging the one capacitor to a maximum-energy state.

21. The device of claim 19, wherein the means for discharging the one or more wet-tantalum capacitors initiates discharge in response to the determined charge time or leakage current falling within a specific range.

22. The device of claim 18, wherein discharging the one wet-tantalum capacitor through the non-therapeutic load comprises discharging the one wet-tantalum capacitor through one or more of the leads at a non-therapeutic level.

23. A method of maintaining one or more capacitors in an implantable medical device, with each capacitor having a rated voltage or a maximum-energy voltage, the method comprising:
maintaining at least one of the capacitors at a high voltage relative its rated voltage or maximum-energy voltage for a time greater than one minute; and
discharging, after the time, the one or more of the capacitors through a non-therapeutic load, wherein discharging includes:
allowing the one of the wet-tantalum capacitors to float for a first time period; and
discharging the one or more of the wet-tantalum capacitors through a non-therapeutic load after expiration of the first time period.

24. The method of claim 23, wherein the the one of the capacitors is a hybrid capacitor or wet-tantalum capacitor.

25. The method of claim 23, wherein the non-therapeutic load is a resistor.

26. A method of maintaining one or more wet-tantalum capacitors in an implantable medical device, with each capacitor having a rated voltage, a tantalum anode, and a non-tantalum cathode, the method comprising:
maintaining at least one of the wet-tantalum capacitors at a voltage equal to about 90% of its rated voltage for a time of greater than or equal to about five minutes;
discharging, after the time, the one or more of the wet-tantalum capacitors through a non-therapeutic load.

27. A method of maintaining one or more wet-tantalum capacitors in an implantable medical device, with each capacitor having a rated voltage or a maximum-energy voltage, the method comprising:

maintaining at least one of the wet-tantalum capacitors at a high voltage relative its rated voltage or maximum-energy voltage for a time; and discharging, after the time, the one of the wet-tantalum capacitors through system leakage.

28. The method of claim 27, wherein the high voltage is about 90 percent of the rated voltage or a maximum-energy voltage for the capacitors.

29. The method of claim 27, wherein the one wet-tantalum capacitor comprises a tantalum anode and a non-tantalum cathode.

30. The method of claim 27, further including determining a value related to a capacitor leakage current, wherein the time is based on the value related to the capacitor leakage current.

31. The method of claim 27, wherein the time is greater than or equal to 15 seconds.

32. The method of claim 27, wherein the implantable device functions as a defibrillator, a cardioverter, or a pacemaker.

33. The method of claim 27, wherein each of the one or more capacitors has a 185-volts surge rating, a first nominal leakage-current rating of about 60 microamps at about 175 volts, a second nominal leakage-current rating of about 90 microamps at about 185 volts, an AC capacitance of about 490 microfarads, and an equivalent-series resistance of about 1.2 ohms.

34. A method of maintaining one or more wet-tantalum capacitors in an implantable medical device, with each capacitor having a rated voltage, the method comprising:

maintaining at least one of the wet-tantalum capacitors at a high voltage relative its rated voltage for a time greater than or equal to 15 seconds;

discharging, after the time, the one or more of the wet-tantalum capacitors through system leakage.

35. The method of claim 34, wherein the high voltage is about 90 percent of the rated voltage.

36. The method of claim 34, wherein the one wet-tantalum capacitor comprises a tantalum anode and a non-tantalum cathode.

37. A method of maintaining one or more wet-tantalum capacitors in an implantable medical device, with each capacitor having a rated voltage, a tantalum anode, and a non-tantalum cathode, the method comprising:

maintaining at least one of the wet-tantalum capacitors at a voltage equal to about 90% of its rated voltage for a time greater than or equal to about five minutes;

discharging, after the time, the one or more of the wet-tantalum capacitors through system leakage.

38. A method of maintaining one or more capacitors in an implantable medical device, with each capacitor having a rated voltage or a maximum-energy voltage, the method comprising:

maintaining at least one of the capacitors at a high voltage relative its rated voltage or maximum-energy voltage for a time greater than one minute; and discharging, after the time, the one or more of the capacitors through system leakage, wherein the the one of the capacitors is a hybrid capacitor or wet-tantalum capacitor.

* * * * *